United States Patent
Virtanen

(10) Patent No.: US 6,190,521 B1
(45) Date of Patent: Feb. 20, 2001

(54) METHOD AND APPARATUS FOR FEEDING A SAMPLE INTO A CAPILLARY ELECTROPHORESIS APPARATUS

(75) Inventor: Rauno Virtanen, Espoo (FI)

(73) Assignee: Valtion Teknillinen Tutkimuskeskus, Vtt (FI)

(*) Notice: Under 35 U.S.C. 154(b), the term of this patent shall be extended for 0 days.

(21) Appl. No.: 09/142,369

(22) PCT Filed: Mar. 6, 1997

(86) PCT No.: PCT/FI97/00149

§ 371 Date: Sep. 4, 1998

§ 102(e) Date: Sep. 4, 1998

(87) PCT Pub. No.: WO97/33166

PCT Pub. Date: Sep. 12, 1997

(30) Foreign Application Priority Data

Mar. 7, 1996 (FI) .......................................... 961069

(51) Int. Cl.[7] .................................................. G01N 27/26
(52) U.S. Cl. ........................................... 204/453; 204/604
(58) Field of Search .................................. 204/451, 453, 204/601, 604

(56) References Cited

U.S. PATENT DOCUMENTS 5,141,621  8/1992  Zare et al. .................... 204/299 R
5,856,100 * 1/1999  Hayashizaki ........................ 435/6

FOREIGN PATENT DOCUMENTS

623819A2   11/1994  (EP) .
2257160A    1/1993  (GB) .

* cited by examiner

Primary Examiner—Jill Warden
Assistant Examiner—Alex Noguerola
(74) Attorney, Agent, or Firm—Pillsbury Madison & Sutro LLP

(57) ABSTRACT

The invention relates to a method and device for introducing a sample into the separation capillary of a capillary zone electrophoresis apparatus, which capillary zone electrophoresis apparatus comprises two reservoirs which contain a background electrolyte solution, the reservoirs being interconnected by a capillary tube which contains background electrolyte solution; electrodes placed in the reservoirs, the electrodes being connected to a high-voltage source; and a detector at the outlet end of the capillary. The sample is injected by means of a fixed or movable sample-injection capillary by placing the sample-injection capillary in the vicinity of the inlet end of the capillary of the capillary zone electrophoresis apparatus in such a manner that the sample solution will surround the said inlet end entirely, and sample is transferred into the separation capillary by means of an electrophoresis electric current or in some other manner, and after a predetermined time the solution is withdrawn from the vicinity of the said inlet end, whereupon the sample solution is replaced by the background solution.

9 Claims, 6 Drawing Sheets

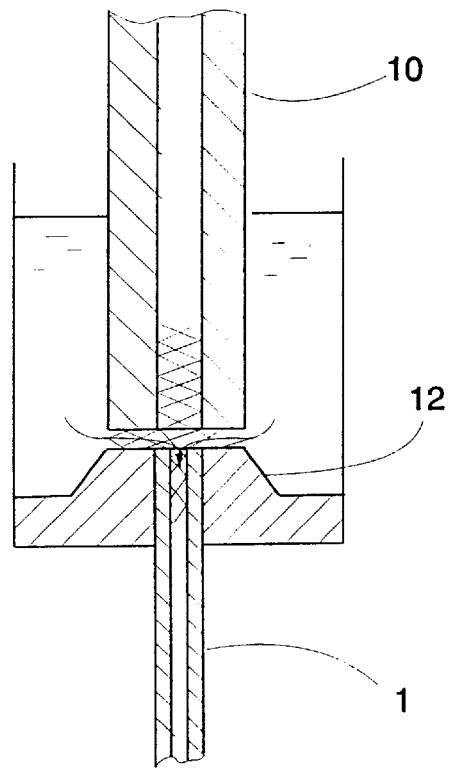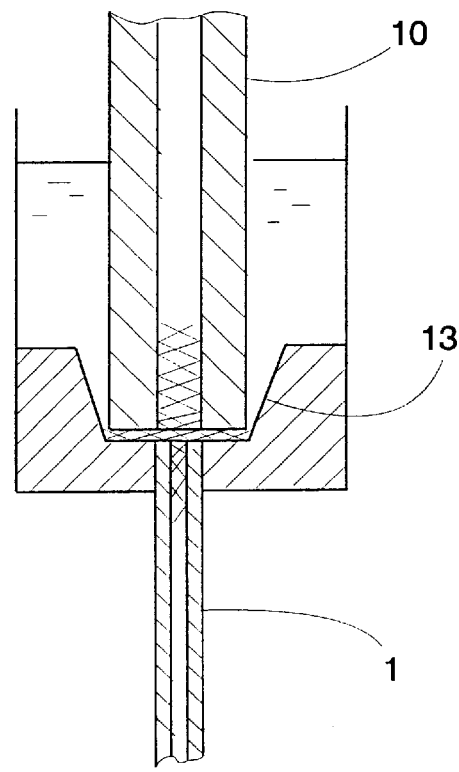
FIG. 5
FIG. 6

METHOD AND APPARATUS FOR FEEDING A SAMPLE INTO A CAPILLARY ELECTROPHORESIS APPARATUS

This application is a national phase of international application PCT/FI97/00149 filed Mar. 6, 1997 which designated the U.S.

BACKGROUND OF THE INVENTION

The invention relates to a method and a device for feeding a liquid sample into the capillary of a capillary electrophoresis apparatus.

Electrophoresis is an electrochemical method by which it is possible to separate electrically charged particles, and by certain special methods also uncharged particles, in an electrolyte solution, the size of the particles varying from the smallest ions and molecules to colloidal particles. The particles migrate in an electric field at different speeds depending on their electrical charge and other properties. In zone electrophoresis, the sample to be separated is placed as a narrow zone in the electrolyte solution, i.e. background solution. In the electric field the various components of the sample become separated as separate zones. In order for the zones not to spread excessively, convection of the background solution must be inhibited. In zone electrophoresis this is done, for example, by stabilizing the solution by paper, gel or some other supporting medium.

The latest stage of electrophoresis development is capillary electrophoresis, which is one of the most rapidly progressing areas of application in analytical chemistry. In this method the background solution is in a narrow or tube, capillary, which is so narrow that the viscous forces of the liquid will inhibit convection. The inner diameter of the capillary usually ranges from 20 to 100 $\mu$m. Electrophoresis is thus performed in a free solution; thereby disturbances caused by a supporting medium are eliminated. It is also easy to eliminate from the capillary the thermal energy generated by the electric current, and thus a high electric field can be applied, thus speeding up separation. Furthermore, automation of capillary electrophoresis is easy.

In capillary zone electrophoresis, two reservoirs containing the background electrolyte solution are interconnected by a capillary tube which contains the same solution. Each reservoir is equipped with an electrode. The sample to be analyzed is introduced as a short zone into one end of the capillary. For the introduction of a sample the end of the capillary is usually transferred into one reservoir, and the desired amount of the sample solution is injected into the capillary, where-after the capillary end is transferred back into the background solution. By means of electrodes in the reservoirs, an electric field is applied on the capillary, usually ranging from 200 to 1000 V/cm, under the effect of which the electrically charged particles will begin to move in the capillary. The different particles will separate from each other if they have different speeds in the electric field. The particle zones will pass a detector at the other end of the capillary at different times, and their signals are measured.

Capillary electrophoresis has many advantages, such as high separation speed, high resolution, and small required sample size. In order to achieve high resolution it is important that the sample can be introduced as a zone as short as possible into the capillary. The capillary volume in itself is very small, and the sample volume must be only a small proportion of the capillary volume. The problem of sample injection in capillary electrophoresis has not been solved satisfactorily. At present there are two methods used for sample introduction, the hydrodynamic method and the electrokinetic method. In both methods the capillary is first filled with a background solution, and for the time of sample injection the samplereceiving end of the capillary is transferred into the sample solution, the amount of which must be sufficient for the capillary end to be immersed in it.

In the hydrodynamic method, the sample is injected into the capillary by a pressure difference. The pressure difference is produced either by placing the capillary ends at different levels, whereby a hydrostatic pressure difference is produced, or in a sealable sample reservoir overpressure is generated by means of gas, the overpressure injecting the sample solution into the capillary. The amount of sample passing into the capillary is controlled by the selection of the pressure difference and its effective time.

In electrokinetic introduction of a sample, a capillary end is placed in the sample reservoir and the electrophoresis current is applied between the electrodes, whereupon the charged particles in the sample will begin to travel into the capillary at speeds depending on their specific mobilities. Furthermore, the entire sample solution will begin to flow into the capillary under the effect of electro-osmosis. The sample amount transferred is a function of the electric field and the time, and it is different for substances with different electric mobilities.

These known sample-introduction methods presuppose that the sample-receiving end of the capillary is transferred from the background solution into the sample solution, and after sampling back into the background solution, and that there is a sufficient amount of the sample. The transfer steps are inconvenient and affect the injected sample amount, and additionally they are to some extent uncontrollable. The mere dipping of the capillary in the sample solution will cause a small amount of sample to be injected. In order for the introduction of the sample to be precisely controllable, it must be performed without moving the capillary out of the background solution.

U.S. Pat. No. 5,141,621 discloses a capillary electrophoresis system wherein the sample-injection capillary and the separation capillary of the electrophoresis apparatus are fixedly linked to an interface chamber. The construction of the interface is difficult and the fixed interface complicates, for example, the replacement of the injection capillary and/or the separation capillary. Furthermore, in the system of the U.S. patent, it is necessary to use pumping for pumping the sample solution through the injection capillary into the interface chamber or into the separation capillary. In this case a much larger amount of the sample is needed than what is introduced into the separation capillary.

BRIEF SUMMARY OF THE INVENTION

It is an object of the present invention to provide a novel method and device for use for introducing a sample into the separation capillary in capillary zone electrophoresis. It is a particular object of the invention to provide a method and device by means of which the sample can be injected into the capillary tube without moving the capillary out of the background solution. In addition, it is an object of the invention to provide a method and device the use of which will not require large amounts of the sample.

The invention has the advantage that the sample-receiving end of the separation capillary need not be moved out of the background solution, and thus the introduction of the sample is sped up and facilitated, and the amount of the sample injected can be controlled with precision. Furthermore, the required sample amount is very small.

The main principle according to which the injection method according to the invention works is as follows. Initially the inlet end of the separation capillary of the capillary zone electrophoresis apparatus is in a pure background solution. Electric current and electro-osmotic flow transfer a homogenous background solution into the capillary. In order to introduce a sample around the inlet end of the capillary, the sample solution is introduced in such a manner that, in the area of the end, the background solution is replaced continuously by the sample solution while contact with the electrodes is maintained. After a selected period the sample solution is withdrawn from the vicinity of the capillary inlet end, and it is replaced by the background solution. The voltage may be on all the time or during selected times. Thus sample zones of precisely the desired size can be introduced into the capillary. Hydrodynamic injection can also be performed according to this principle.

BRIEF DESCRIPTION OF THE DRAWINGS

The invention is described below in detail, with reference to the accompanying drawings, wherein

FIG. 5 depicts another embodiment of the sample-injection capillary according to the invention;

FIG. 6 depicts one further embodiment of the sample-injection capillary according to the invention;

DETAILED DESCRIPTION OF THE INVENTION

Figure 1:
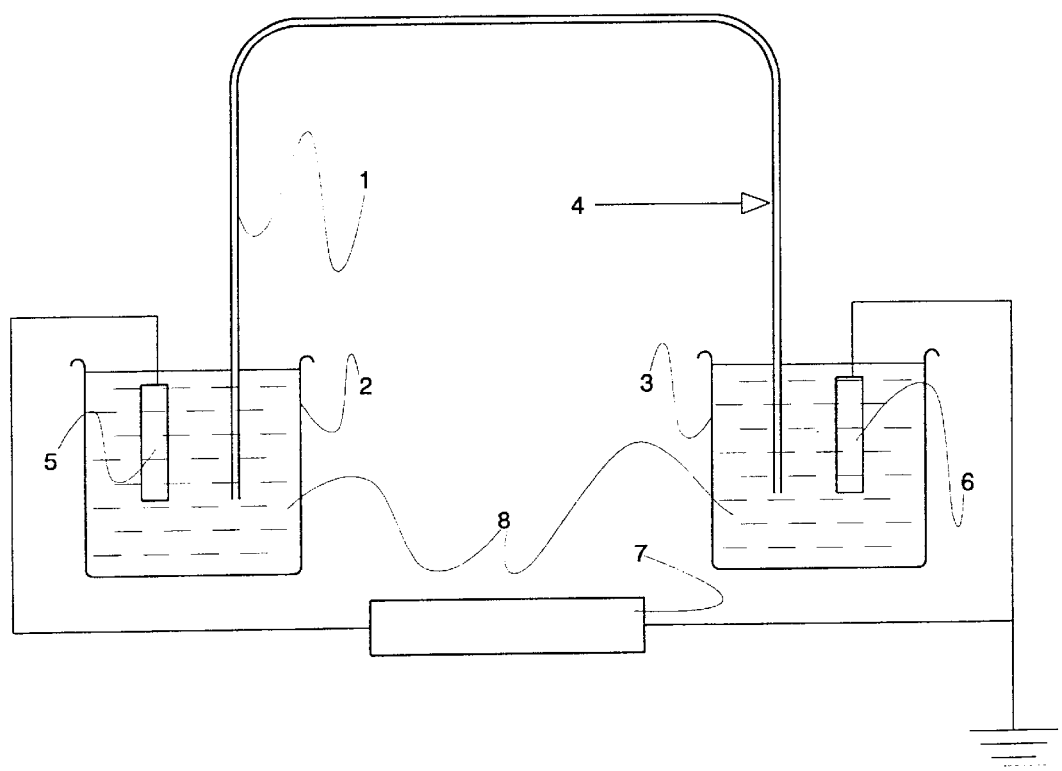
FIG. 1 depicts the principle of capillary zone electrophoresis.

FIG. 1 shows the general principle of capillary zone electrophoresis. Each end of the separation capillary 1 is placed in a reservoir 2 and 3, which contain the background electrolyte solution 8. The reservoirs have electrodes 5 and 6, which are connected to a high voltage source 7. In addition, in connection with the outlet end of the separation capillary 1 there is mounted a detector 4, by means of which the particles separated in the capillary are detected. The detection can be performed, for example, on the basis of the absorbance of the sample. The sample travels through the capillary 1 past the detector 4 into the reservoir 3. The inner diameter of the separation capillary is typically approx. 25–100 $\mu$m.

Figures 2A, 2B, 2C:
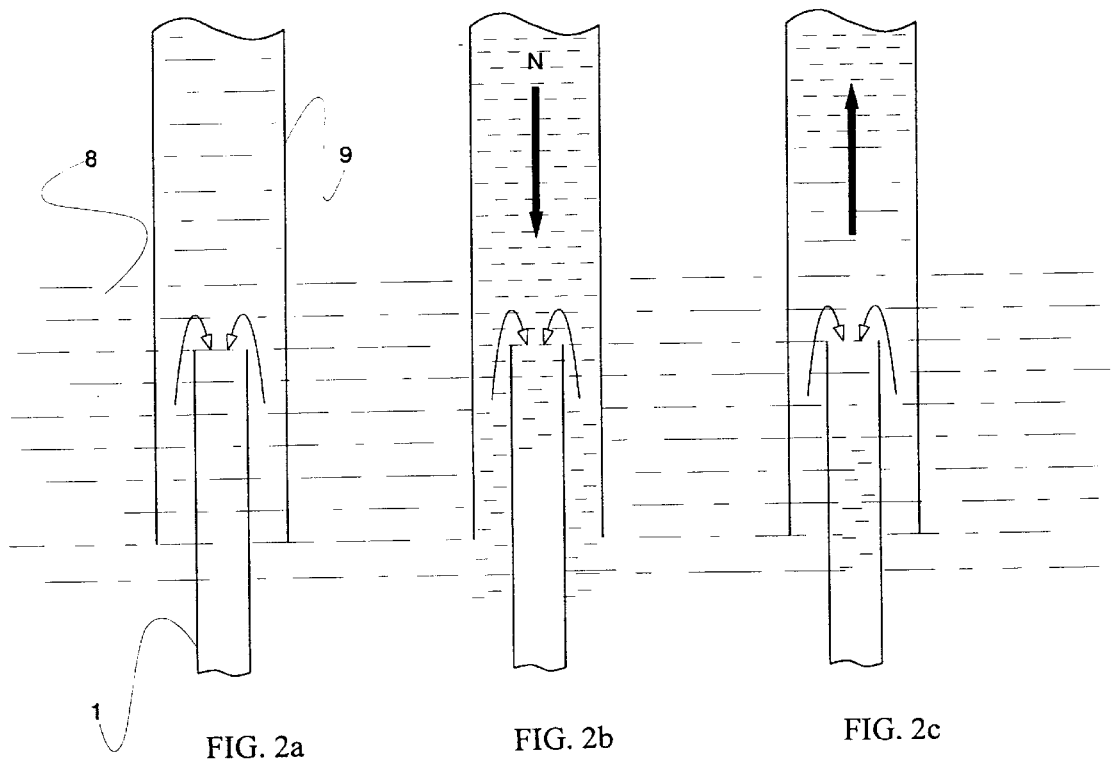
FIGS. 2a, 2b and 2c and depict a sample injection device according to the invention, having a fixed sample injection capillary.

In FIGS. 2, a, b and c, there is shown an embodiment of the invention in which the sample solution (N) is introduced into the vicinity of the capillary inlet end by means of a fixed sample-injection capillary 9, the inner diameter of which is greater than the outer diameter of the inlet end of the capillary 1 of the capillary zone electrophoresis apparatus. The difference between the said diameters of the capillaries is typically approx. 0.1–1 mm. In FIG. 2, a, the end of the sample-injection capillary 9 is placed around the inlet end of the said separation capillary 1 in such a way that the ends overlap one inside the other. At this stage the sample-injection capillary end in contact with the background solution may be full of the background solution. In b, it is shown how the sample solution (N) contained in the sample-injection capillary entirely surrounds the said inlet end, the background solution having been entirely replaced by the sample solution around the inlet end of the separation capillary 1. The sample is introduced for a predetermined time, whereafter, in c, the sample solution is withdrawn from around the inlet end of the separation capillary by means of suction via the sample-injection capillary 9, whereupon the sample solution is again replaced by the background solution 8. In the figure, the thinner arrows depict the direction of the electric current and the electro-osmotic flow, and the thicker arrows depict the travel direction of the sample solution in the sample-injection capillary.

Figures 3A, 3B, 3C:
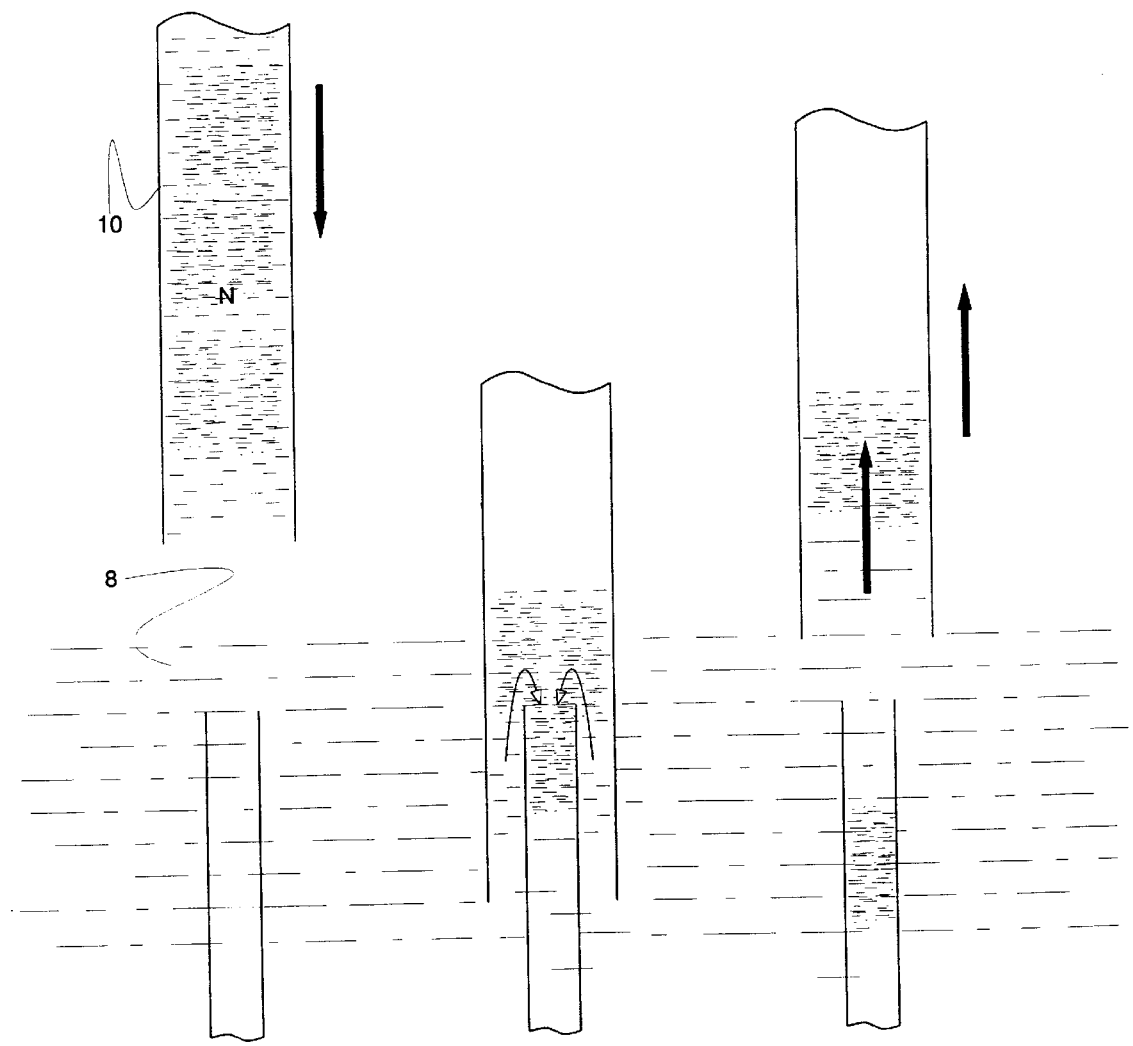
FIGS. 3a, 3b and 3c depict a sample injection device according to the invention, having a movable sample-injection capillary.

FIGS. 3, a, b and c, shows an embodiment according to the invention in which the sample solution (N) is introduced into the vicinity of the inlet end of the separation capillary 1 by means of a movable sample-injection capillary 10, the inner diameter of which is greater than the outer diameter of the inlet end of the separation capillary 1 of the capillary zone electrophoresis apparatus. The difference between the said diameters of the capillaries is typically approx. 0.1–1 mm. In a, the injection capillary, filled with the sample, is ready for being lowered into the injection position. The electrophoresis voltage is on, and the background solution is flowing into the separation capillary. In b, the sample-injection capillary is being introduced around the inlet end of the separation capillary 1 in the background solution in such a manner that the ends will overlap one inside the other, whereupon the background solution will be replaced by the sample solution around the inlet end of the capillary 1. The sample is transferred into the separation capillary by means of the electrophoresis current. The sample is injected for a predetermined time, whereafter, in c, the sample-injection capillary 10 is withdrawn from around the inlet end of the separation capillary. At the same time, sample solution may be sucked backwards in the injection capillary in order to avoid contamination of the background solution. This is not, however, necessary, since the background solution can be maintained pure in a manner independent of the injection system. The amount of the sample transferred into the separation capillary is determined by the speed of the electro-osmotic flow, the electrophoresis current and the injection time. The thinner arrows in the figure depict the direction of the electric current and the electro-osmotic flow, and the thicker arrows depict the travel direction of the sample solution in the sample-injection capillary and the movement of the sample-injection capillary.

Figures 4A, 4B, 4C:
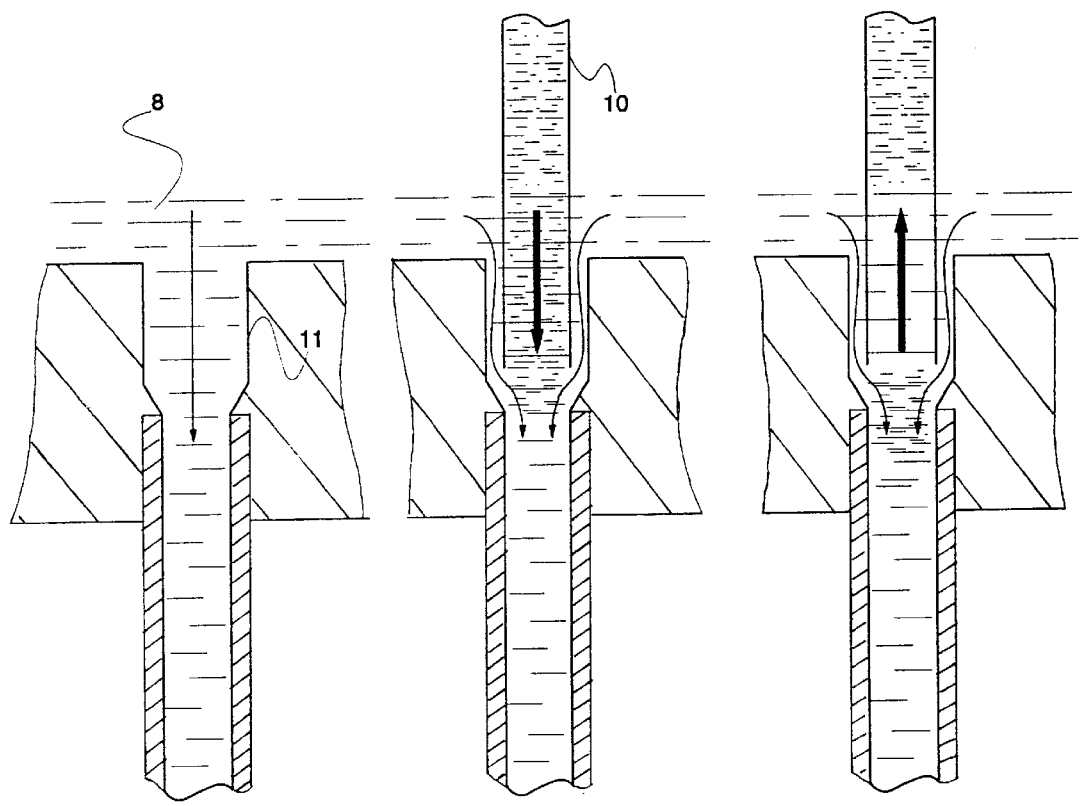
FIGS. 4a, 4b and 4c depict one embodiment of the movable sample-injection capillary according to the invention.

FIGS. 4, a, b and c, shows an embodiment of the invention in which the sample solution (N) is introduced into the vicinity of the inlet end of the capillary 1 by means of a movable sample-injection capillary 10. The sample-injection capillary 10 may also be fixedly mounted. In this embodiment, in the bottom of the electrode reservoir, in front of the inlet end of the separation capillary 1, there is a conduit 11 having a diameter greater than the outer diameter of the injection capillary.

In FIG. 4, b, the movable sample-injection capillary which contains sample solution is brought to the vicinity of the inlet end of the separation capillary in conduit 11 in such a manner that it will not block communication between the inlet end of the separation capillary 1 and the background solution. In b, the sample solution is being injected so that it will entirely fill the surroundings of the inlet end of the capillary 1. The sample will be transferred into the separation capillary 1 by means of either electric current and electro-osmotic flow or suction generated at the other end of the capillary. The sample is injected for the desired time, whereafter, in c, the sample-injection capillary 10 is withdrawn from the vicinity of the inlet end of the separation capillary. At the same time, solution may be sucked via the injection capillary in order to maintain the purity of the background solution in the electrode reservoir. However, this is not necessary, since, if it is to be expected that the background solution will be contaminated, it can be maintained pure in a manner independent of the feeding system. The thinner arrows in the figure depict the direction of the electric current and the electro-osmotic flow, and the thicker arrows depict the travel direction of the sample solution in the sample-injection capillary and the movement of the sample-injection capillary.

In the embodiment of the invention shown in FIG. 5, the upper end of the separation capillary 1 has been mounted so that its upper edge is at the same level as the bottom of the background solution reservoir. In the bottom of the background solution reservoir there is a protrusion 12 constituting part of the bottom. A movable sample-injection capillary 10 has been lowered into the injection position, and into the surroundings of the inlet of the separation capillary 1 there has been injected sample solution, which is beginning to flow into the separation capillary under the effect of the electrophoresis current. After a suitable time, any excess sample solution may be sucked off via the sample-injection capillary 10 or in some other manner.

In FIG. 6, there is, in the bottom of the background solution reservoir, a depression 13 which constitutes part of the bottom, this depression guiding the movement of the sample-injection capillary 10. The upper edge of the separation capillary end is at the same level as the bottom of the depression. The injection of the sample is performed as in FIG. 5. In the embodiments of FIGS. 5 and 6 the inner diameter of the injection capillary is substantially equal to or slightly greater than the inner diameter of the separation capillary.

Figure 7A:
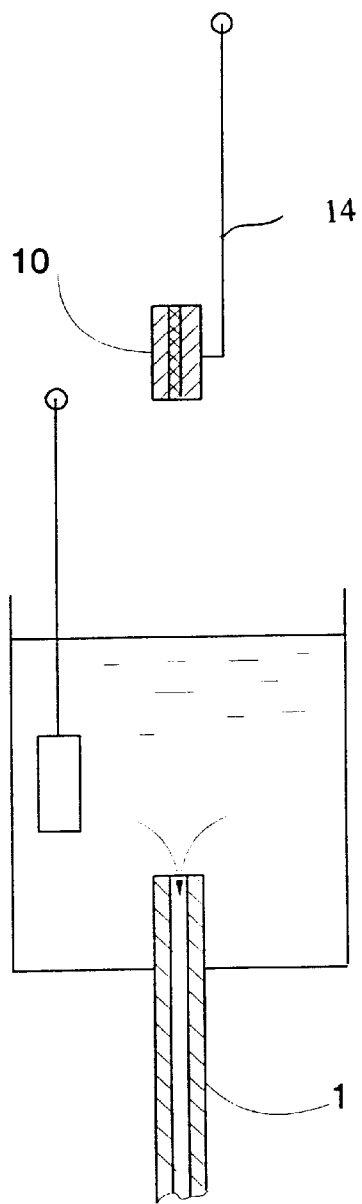
FIGS. 7a and 7b depict an embodiment of the movable sample-injection capillary according to the invention, wherein a short sample-injection capillary is immersed in its entirety in a reservoir containing the background electrolyte.
Figure 7B:
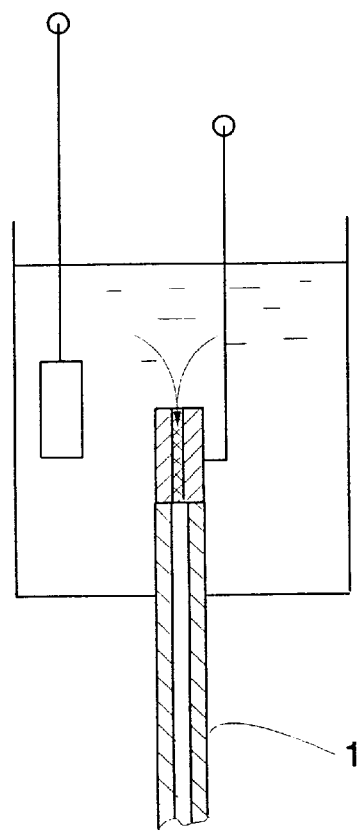

In FIG. 7, a, the injection capillary 10, equipped with an arm 14, is, filled with the sample, ready for being lowered into the injection position. The electrophoresis voltage is on, and background solution is flowing into the separation capillary 1. The arrows depict the flow. In b, the injection capillary 10 has been lowered to the inlet of the separation capillary 1 in such a manner that the ends of the capillaries are against each other. The injection capillary 10 is so short that it will be completely immersed in the background solution, typically for example 2–10 mm. The sample is transferred into the separation capillary by means of the electrophoresis current. In the embodiment of FIG. 7, the ratio of the inner diameter of the injection capillary to the inner diameter of the separation capillary may typically range from 0.1 to 2. By the selection of a smaller inner diameter for the injection capillary, a smaller sample volume is obtained. The sample volume may also be affected by the length of the injection capillary.

What is claimed is:

1. A method for introducing a sample into the separation capillary of a capillary zone electrophoresis apparatus comprising two reservoirs which contain a background electrolyte solution, the reservoirs being interconnected by a separation capillary which contains background electrolyte solution, electrodes located in the reservoirs, the electrodes being in contact with a high-voltage source; and a detector at the outlet end of the capillary, comprising:

introducing the sample by means of a fixed or movable sample-injection capillary placing the sample-injection capillary in the vicinity of the inlet an end of the separation capillary of the capillary zone electrophoresis apparatus in such a manner that the sample solution being in the sample-injection capillary, or being injected therefrom, will surround the said inlet end entirely, and withdrawing, after a predetermined times the sample-injection capillary from the vicinity of the inlet end of the separation capillary of the capillary zone electrophoresis apparatus, whereupon the sample solution will be replaced by the background solution.

2. A method according to claim 1, wherein the sample-injection capillary is fixed, and its inner diameter is greater than the outer diameter of the inlet end of the separation capillary of the capillary zone electrophoresis apparatus, and the end of the sample-injection capillary is placed around the said inlet end in such a manner that the ends will overlap one inside the other, and after a predetermined time the sample solution is withdrawn from around the inlet end of the separation capillary of the capillary zone electrophoresis apparatus.

3. A method according to claim 1, wherein the sample-injection capillary is movable, and its inner diameter is greater than the outer diameter of the inlet end of the separation capillary of the capillary zone electrophoresis apparatus, and the end of the sample-injection capillary is placed around the said inlet end in such a manner that the ends will overlap, one inside the other, and after a predetermined time the sample-injection capillary is withdrawn from around the inlet end of the separation capillary of the capillary zone electrophoresis apparatus.

4. A method according to claim 1, wherein the inlet end of the separation capillary of the capillary zone electrophoresis apparatus is in fixed contact with a conduit formed in the bottom of the electrode reservoir, the diameter of the conduit being greater than the diameter of the sample-injection capillary, and the movable sample-injection capillary is introduced inside the conduit, into the vicinity of the inlet end of the separation capillary of the capillary zone electrophoresis apparatus, and after a predetermined time the sample-injection capillary is withdrawn from the vicinity of the said inlet end.

5. A method according to claim 1, wherein the inlet end of the separation capillary of the capillary zone electrophoresis apparatus is in fixed contact with a conduit formed in the bottom of the electrode reservoir, the diameter of the conduit being greater than the diameter of the sample-injection capillary, and a fixed sample-injection capillary is placed in the vicinity of the inlet end of the separation capillary of the capillary zone electrophoresis apparatus, and after a predetermined time the sample is withdrawn from the vicinity of the said inlet end.

6. A method according to claim 1, wherein the upper edge of the upper end of the separation capillary of the capillary zone electrophoresis apparatus is mounted at the same level as the upper edge of a protrusion formed in the bottom of the background solution reservoir, and the end of a movable sample-injection capillary is introduced into the vicinity of the inlet end of the separation capillary, and after a predetermined time the sample-injection capillary is withdrawn from the vicinity of the same inlet end.

7. A method according to claim 1, wherein the upper edge of the upper end of the separation capillary of the capillary zone electrophoresis apparatus is mounted at the same level as the bottom of a depression formed in the bottom of the background solution reservoir, and the end of a movable sample-injection capillary is introduced into the vicinity of the inlet end of the separation capillary, and after a predetermined time the sample-injection capillary is withdrawn from the vicinity of the said inlet end.

8. A method according to claim 1, wherein an end of the sample-injection capillary equipped with an arm is introduced into the vicinity of the inlet end of the separation capillary in such a manner that the ends of the capillaries will be against each other, and that the injection capillary is completely immersed in the background solution, and after a predetermined time the sample-injection capillary is withdrawn from the vicinity of the said inlet end.

9. A device for introducing a sample into a separation capillary of a capillary zone electrophoresis apparatus, the capillary zone electrophoresis apparatus comprising:

two reservoirs which contain a background electrolyte solution, the reservoirs being interconnected by a separation capillary which contains background electrolyte solution; electrodes placed in the reservoirs, the electrodes being in contrast with a high-voltage source; and a detector at an outlet end of the separation capillary; and a movable or fixed sample-injection capillary which contains a sample solution, wherein the inlet end of the separation capillary of the capillary zone electrophoresis apparatus is in fixed contact with a conduit formed in the bottom of the electrode reservoir, the diameter of the conduit being greater than the diameters of the sample-injection capillary and the capillary (1) of the capillary zone electrophoresis apparatus.

* * * * *